United States Patent [19]
Kontos

[11] Patent Number: 6,022,372
[45] Date of Patent: Feb. 8, 2000

[54] ARTERIAL STAPLING DEVICE

[75] Inventor: Stavros Kontos, Woodcliff Lake, N.J.

[73] Assignee: X-Site, L.L.C., Totowa, N.J.

[21] Appl. No.: 09/174,396

[22] Filed: Oct. 14, 1998

Related U.S. Application Data

[62] Division of application No. 08/799,667, Feb. 11, 1997, Pat. No. 5,861,005.

[51] Int. Cl.[7] ......................................... A61B 17/10
[52] U.S. Cl. .................. 606/219; 606/139; 227/175.1
[58] Field of Search .................................. 606/213, 215, 606/216, 217, 218, 219, 139; 227/175.1, 178.1, 181.1, 901

[56] References Cited

U.S. PATENT DOCUMENTS

| | | |
|---|---|---|
| 4,038,985 | 8/1977 | Chiulli . |
| 4,327,709 | 5/1982 | Hanson et al. . |
| 4,832,688 | 5/1989 | Sagae et al. . |
| 4,852,568 | 8/1989 | Kensey . |
| 5,383,896 | 1/1995 | Gershony et al. . |
| 5,403,326 | 4/1995 | Harrison et al. ............... 606/139 |
| 5,484,449 | 1/1996 | Amundson et al. . |
| 5,496,332 | 3/1996 | Sierra et al. . |
| 5,499,995 | 3/1996 | Teirstein . |
| 5,527,322 | 6/1996 | Klein et al. . |
| 5,549,633 | 8/1996 | Evans et al. . |
| 5,575,771 | 11/1996 | Walinsky . |
| 5,613,974 | 3/1997 | Andreas et al. . |
| 5,674,231 | 10/1997 | Green et al. ............... 606/142 |
| 5,732,872 | 3/1998 | Bolduc et al. ............... 227/176.1 |
| 5,855,312 | 1/1999 | Toledano ............... 227/176.1 |
| 5,868,760 | 2/1999 | McGuckin, Jr. ............... 606/139 |
| 5,881,943 | 3/1999 | Heck et al. ............... 227/176.1 |

*Primary Examiner*—Michael Buiz
*Assistant Examiner*—Tina T. D. Pham
*Attorney, Agent, or Firm*—Kenyon & Kenyon

[57] ABSTRACT

A method and device for efficiently and effectively stapling an opening in an anatomical structure such as veins, arteries, organs, and other body members within a living body is disclosed. The opening may be from a deliberately placed incision, as from an invasive surgical procedure, or caused by other damaging events. The device includes a stapling mechanism having a main body with a handle, a trigger for activating the staples, and a central passage through which a balloon catheter may pass. The balloon catheter supports the artery and helps position the stapling mechanism properly on the artery. Alternatively, the device may have a main body that has an inflatable member attached to it and extending from it. The main body provides a passage through which a pressurized media such as saline can be supplied to the inflatable member. In either case, the main body may advantageously include a flashback lumen through which blood or other fluid may flow as an indication of the position of the device within the anatomical structure.

16 Claims, 18 Drawing Sheets

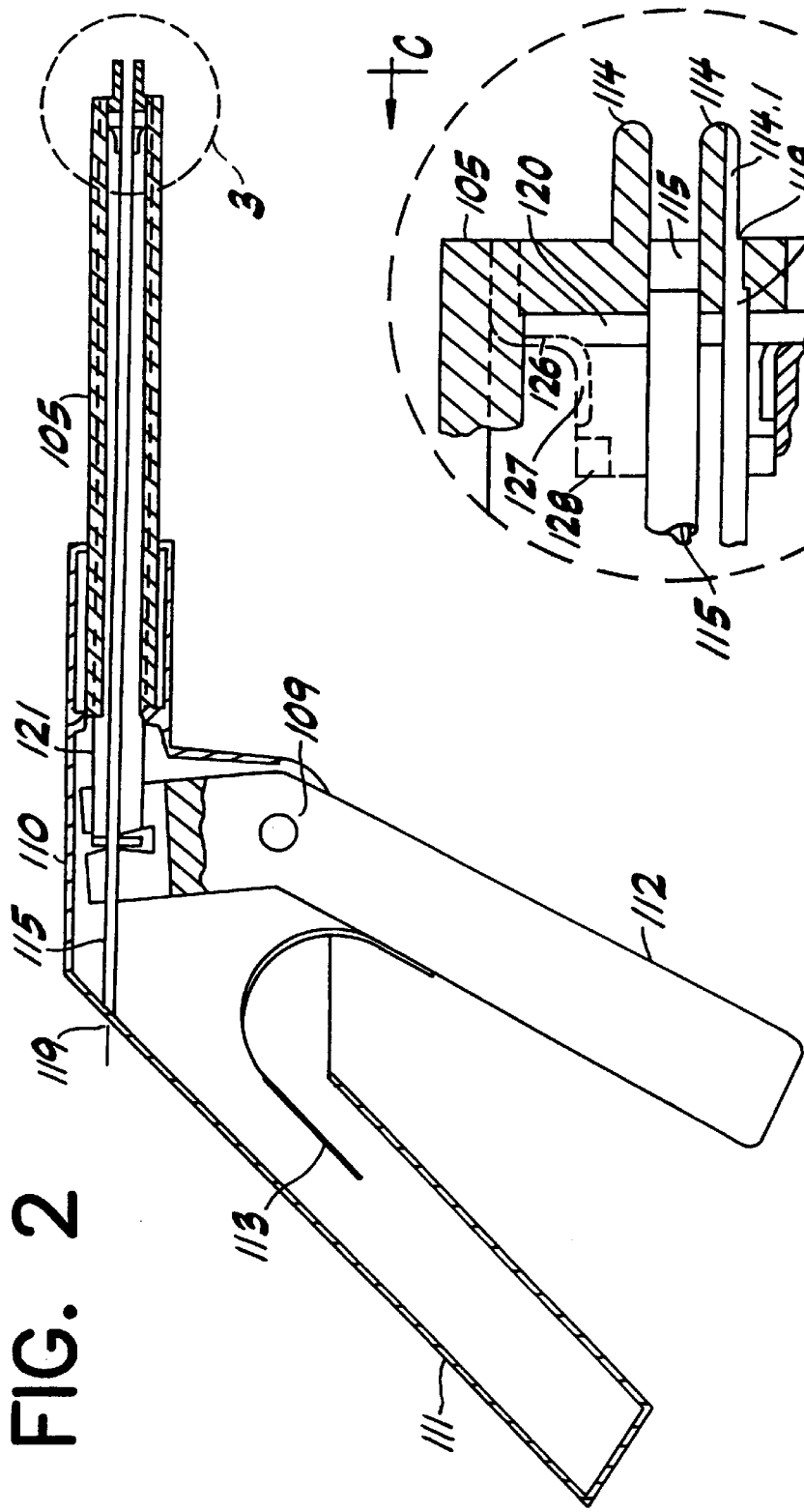
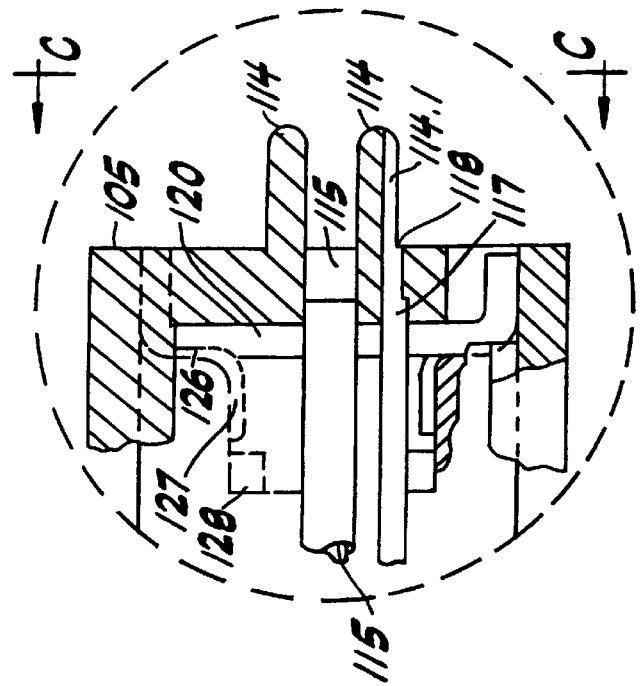
FIG. 2
FIG. 3

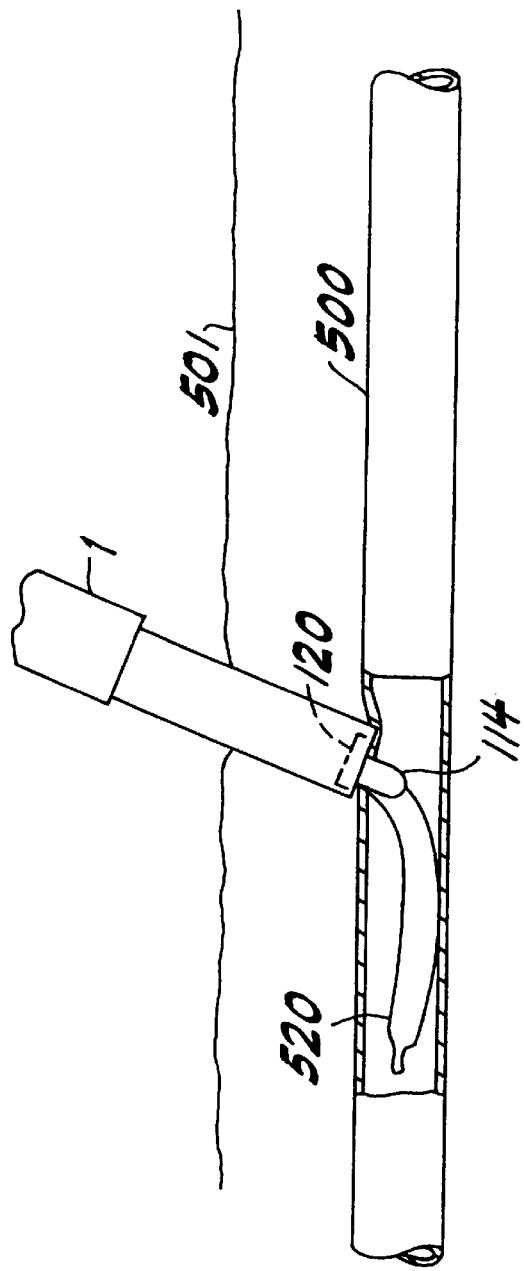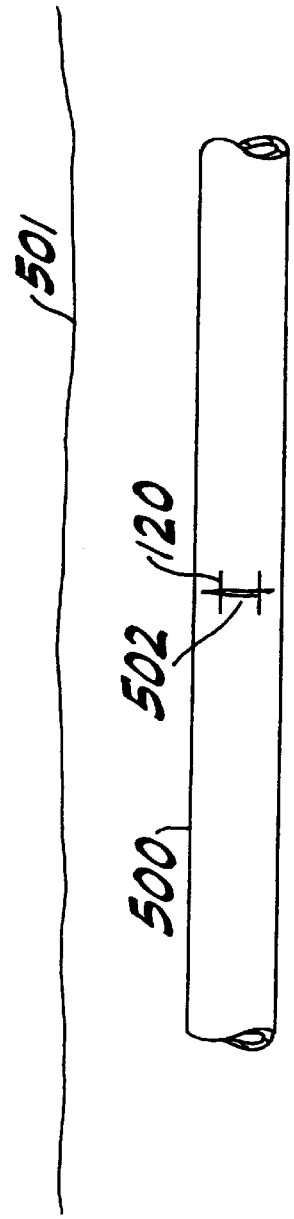
FIG. 11
FIG. 13

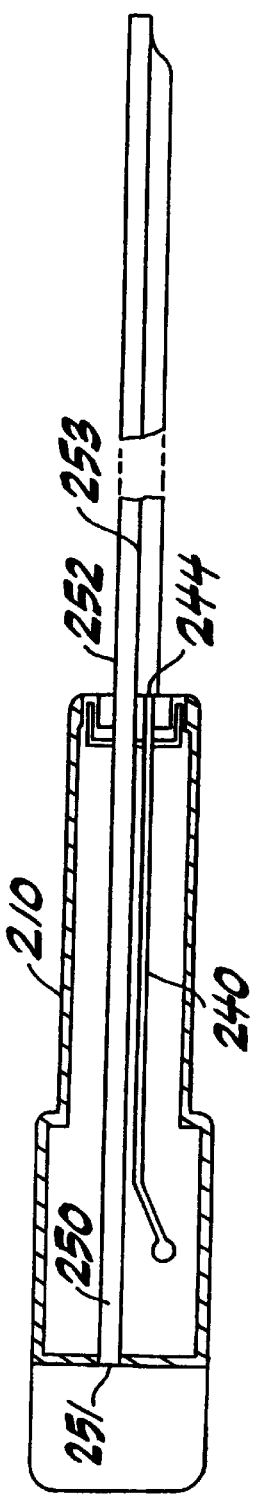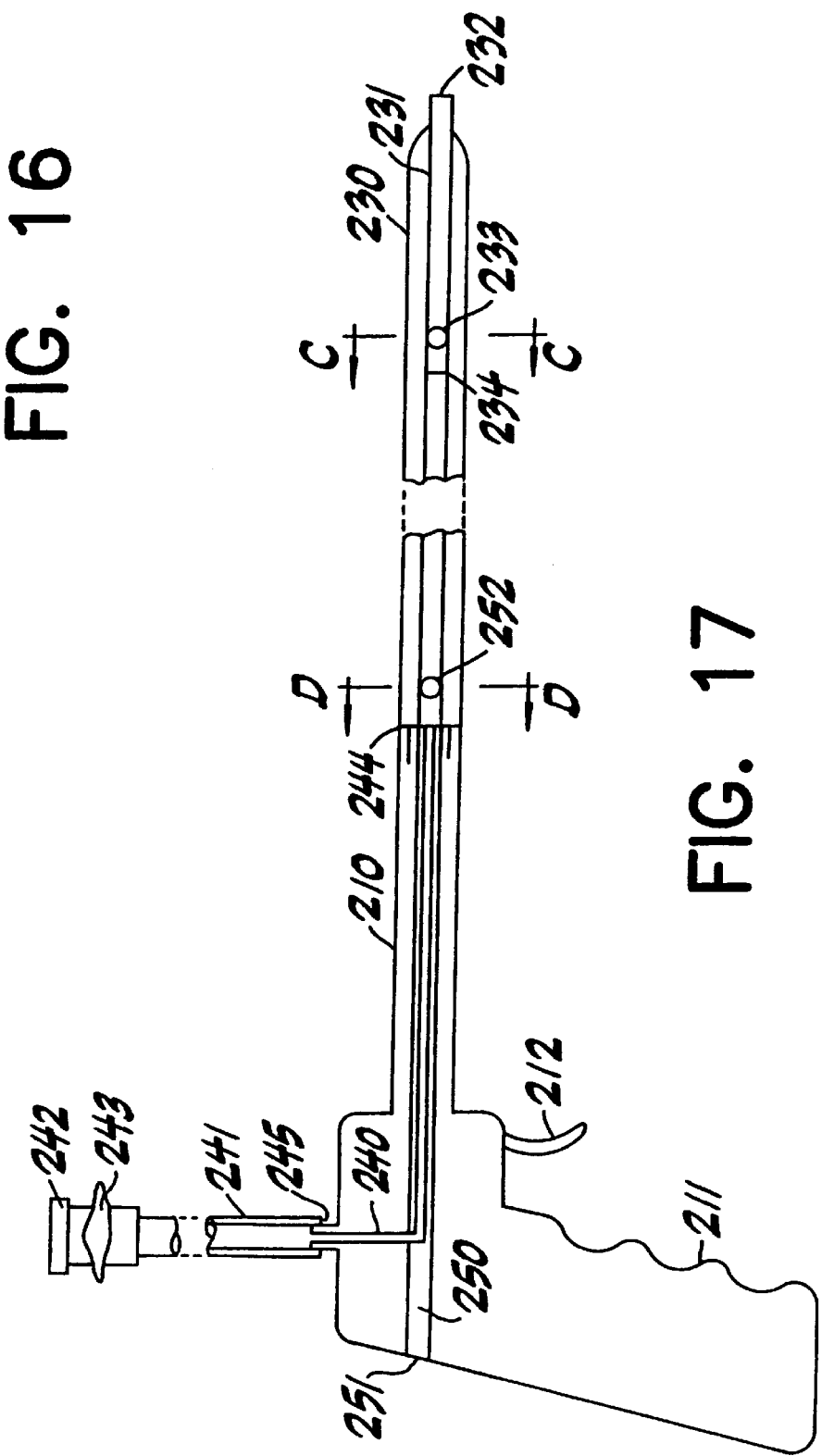
FIG. 16
FIG. 17

ARTERIAL STAPLING DEVICE

This application is a division of prior application Ser. No. 08/799,667, filed Feb. 11, 1997 and now U.S. Pat. No. 5,861,005.

FIELD OF THE INVENTION

The present invention relates to the field of surgical instruments and more particularly to devices for installing surgical staples in vessels, arteries, organs, and the like.

BACKGROUND OF THE INVENTION

Many surgical procedures require the insertion of catheters and/or surgical devices into blood vessels and other internal structures. For example, in the treatment of vascular disease, it is often necessary to insert an instrument, i.e., a catheter, into the blood vessel to perform the treatment procedure. Such treatment procedures often involve piercing a wall of the blood vessel, inserting an introducer sheath into the blood vessel via the opening, and maneuvering the procedural catheter through the introducer sheath to a target location within the blood vessel. Of course in order to complete such a procedure, the sides of the opening in the wall of the blood vessel must be sealed to prevent bleeding while facilitating healing of the wound. At present, this sealing is commonly accomplished by application of direct pressure over the puncture site by a physician or other trained medical professional. Due to the dangers of thrombosis, the substantial reduction of blood flow through the blood vessel due to the application of pressure is undesirable and potentially dangerous to the patient. In addition, the procedure is time consuming; often requiring that pressure be applied for forty-five minutes or more to achieve acceptable sealing.

Other sealing techniques include the application of a biogenic sealing material over the opening to seal the wound. However, proper placement of the sealing material is difficult to achieve and, the plug of sealing material left inside the blood vessel may result in serious health risks to the patient.

As a result, devices have been developed which are inserted through the puncture in order to suture openings created in blood vessels. However, these devices suffer from various drawbacks.

For example, U.S. Pat. No. 5,417,699 to Klein et al. describes a device wherein two needles coupled to a distal end of an insertion shaft are held within an outer shaft during insertion into an internal structure. Once inside the internal structure, the inner shaft is drawn proximally relative to the outer shaft, so that the needles are simultaneously drawn through the walls of the internal structure. The needles are then removed from the device, the device is removed and sutures attached to the needles are tied together to seal the opening. The device of Klein et al., includes no means for ensuring that the device is properly located, is costly to manufacture, and is cumbersome, requiring three hands for operation.

OBJECTS AND SUMMARY OF THE INVENTION

The present invention is directed to an arterial stapling device for sealing a hole in a wall of an anatomical structure within a living body which provides a housing extending from a distal end to a proximal portion, the housing including a catheter receiving lumen extending therethrough from a first opening formed in the proximal portion to a second opening formed in the distal end, wherein when the device is in an operative position with a catheter extending through the catheter receiving lumen and into the hole, the distal end is located within the living body adjacent to the hole and the proximal portion remains outside the living body. The housing further defines at least a first staple orifice in the distal end adjacent to the second opening so that, when the device is in the operative position, the first staple orifice extends across a portion of the hole. The device further includes a stapling mechanism mounted within the housing adjacent to the first staple orifice, and an actuating mechanism coupled between the proximal end of the housing and the stapling mechanism for operating the stapling mechanism so that a staple is ejected from the first staple orifice.

The present invention is also directed to a method of sealing a hole in an anatomical structure within a living body including the steps of:

inserting an apparatus for sealing a hole in a wall of an anatomical structure into a desired position within the living body wherein the apparatus includes an inflatable structure which, when the device is in the desired position, extends from a housing of the apparatus into the hole and, wherein the apparatus further includes a stapling mechanism which, when the device is in the desired position, is located adjacent to the opening;

inflating the inflatable member to seal the hole;

operating the stapling mechanism to place at least one staple into the wall of the anatomical structure across a portion of the opening wherein the stapling mechanism operates to form the staple into a sealing configuration that draws the sides of the hole together to seal the hole; and withdrawing the apparatus from the living body.

BRIEF DESCRIPTION OF THE DRAWINGS

FIG. 2 is a cross-sectional side view of the device shown in FIG. 1 through section A—A.

FIG. 3 is a detail view of the distal end of the device shown in FIG. 2.

FIG. 11 shows a distal portion of the first embodiment of the invention in an operative position within a living body.

FIG. 13 shows a puncture site stapled according to the invention.

FIG. 16 is a top view of the device shown in FIG. 15 through section A—A.

FIG. 17 is a side view of the device shown in FIG. 15 through section B—B.

DETAILED DESCRIPTION OF THE INVENTION

Figure 1:
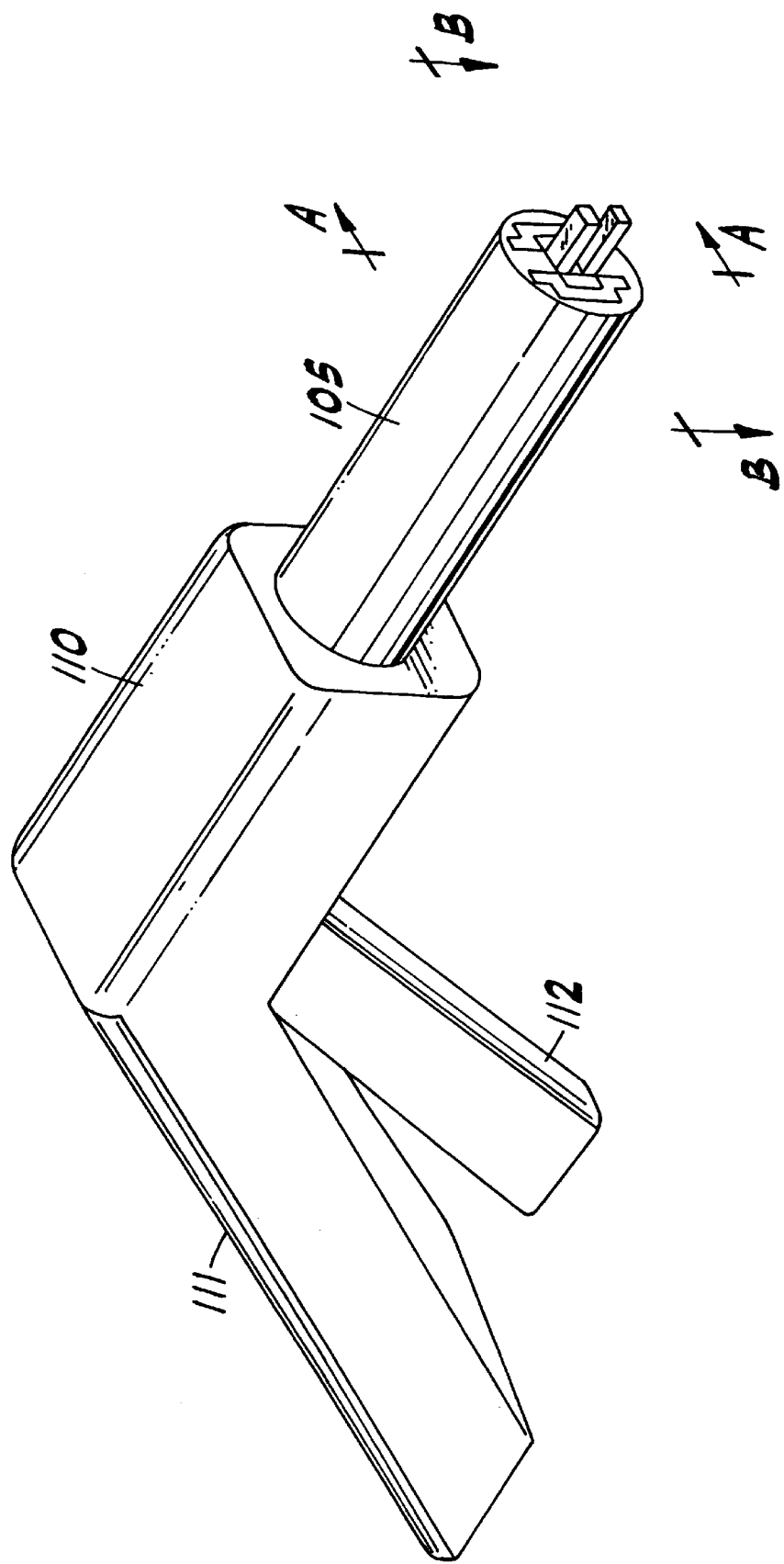
FIG. 1 is a perspective view of a first embodiment of the arterial stapling device of the present invention.

FIG. 1 shows a preferred embodiment of the invention designated generally by the numeral 1. Device 1, which comprises a main body 110, works in conjunction with a balloon catheter (not shown in FIG. 1). Main body 110 has, at its proximal end, a handle 111 and trigger 112 and at its distal end, a tubular projection 105. The distal end of tubular projection 105 may, preferably include optional tabs 114 protruding distally therefrom which serve to hold a balloon catheter in an oval shape. For example, if a balloon catheter having a preformed oval shape is employed, then tabs 114 may be omitted. Further, tabs 114 may be releasably attached to the main body 110 so that, when a user feels these tabs might inhibit proper closing of the artery puncture site, they may be removed.

As shown in FIG. 2, a trigger 112 is rotatably attached to handle 111 for rotation about point 109. A trigger spring 113 biases the trigger 112 toward a cocked or ready position in which the trigger 112 is spaced from the handle 111 (as shown in FIG. 2). Activating or squeezing trigger 112 rotates trigger 112 about rotation point 109 toward the handle 111, thereby advancing staple pushers 121. As staple pushers 121 are advanced, they bend the staples 120 into their binding position as is known in the art, and eject the staples from the distal end of main body 110. When released, trigger 112 is moved back to the ready position by trigger spring 113.

Figure 10:
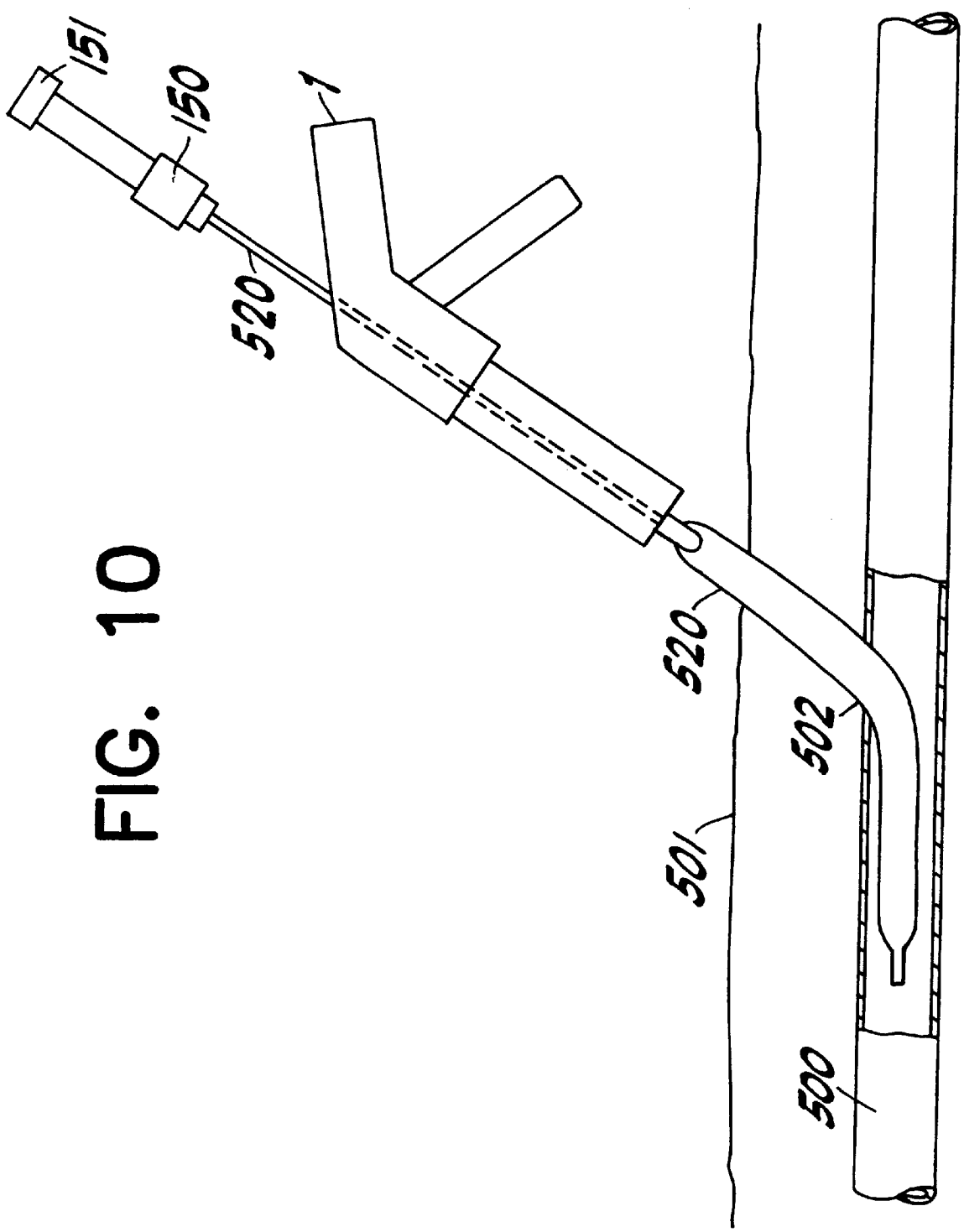
FIG. 10 shows the first embodiment of the invention in its environment of use.

A balloon insertion lumen 115 extends through main body 110 from its proximal to its distal end. As shown in FIG. 10 and discussed in more detail in the description thereof, a balloon catheter which has previously been inserted through a puncture into an artery may be received within the balloon insertion lumen 115 so that the device 1 may be advanced over the balloon catheter until the device 1 reaches a desired position relative to the artery. Main body 110 contains a flashback lumen 117, extending from a blood entry port 118 at the distal end of main body 110 (see FIG. 3) to a blood exit port 119 located proximal to blood entry port 118. By observing blood flow (or the lack thereof) through the flashback lumen 117, the user may determine when the device 1 is in the desired position relative to the artery.

As shown in FIG. 3, tabs 114 extend distally from the distal end of the tubular projection 105. The balloon insertion lumen 115 is located between tabs 114. The blood entry port 118 of the flashback lumen 117 is located adjacent to one of the tabs 114. Through the blood entry port 118, blood or fluid from the artery or anatomical structure may enter flashback lumen 117 and traverse therethrough until reaching blood exit port 119. The tab 114 adjacent to the blood entry port 118 may be advantageously shaped to facilitate passage of blood into the blood entry port. For example, as shown in FIG. 3, a groove 114. 1, which leads to the blood entry port 118, is formed in one of the tabs 114.

A substantially U-shaped staple 120 is shown at the distal end of main body 110. Of course, those skilled in the art will recognize that staples of any shape may be employed with this device so long as the staple pushers 121 are modified accordingly. The u-shape of staple 120 represents a staple prior to placement. Staple pusher 121 which bends and places staple 120 due to the functionally stylized shape of staple pusher 121, includes lateral grooves 126, longitudinal grooves 127, and ramps 128 at its distal end adjacent staples 120.

Figure 4:
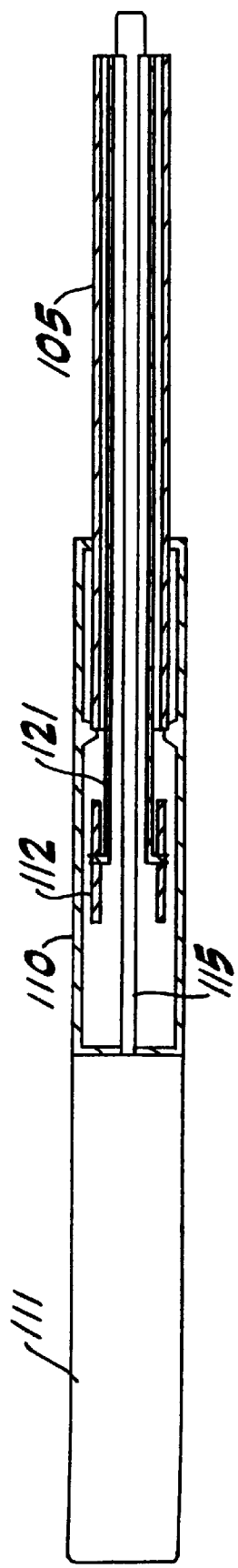
FIG. 4 is a top view of the device shown in FIG. 1 through section B—B.

Staple pushers 121 are connected to trigger 112 at the proximal end of device 1 and extend longitudinally to the distal end of device 1. As shown in FIG. 4, balloon insertion lumen 115 extends from the proximal to the distal end of main body 110. In the embodiment shown in FIG. 4, two staple pushers 121 are located substantially symmetrically on each side of balloon insertion lumen 115. Activation of trigger 112 pushes both staple pushers 121 simultaneously, thus, simultaneously placing two staples 120 into the artery. Those skilled in the art will recognize that, for use with different size arteries, devices of various sizes may be employed having any number of staple pushers 121—one staple pusher 121 for very thin arteries with the number of staple pushers increasing as the diameter of the artery increases. Large arteries may advantageously be stapled by a device having 3 or more staple pushers 121 activated simultaneously to place three staples 120. A further embodiment of the invention may include two independent triggers 112 each attached to an independent staple pusher 121 or pair of staple pushers, to thereby allow a user to place one or more staples independently of other staples. This would permit manipulation of the device between placement of the staples 120.

Figure 5:
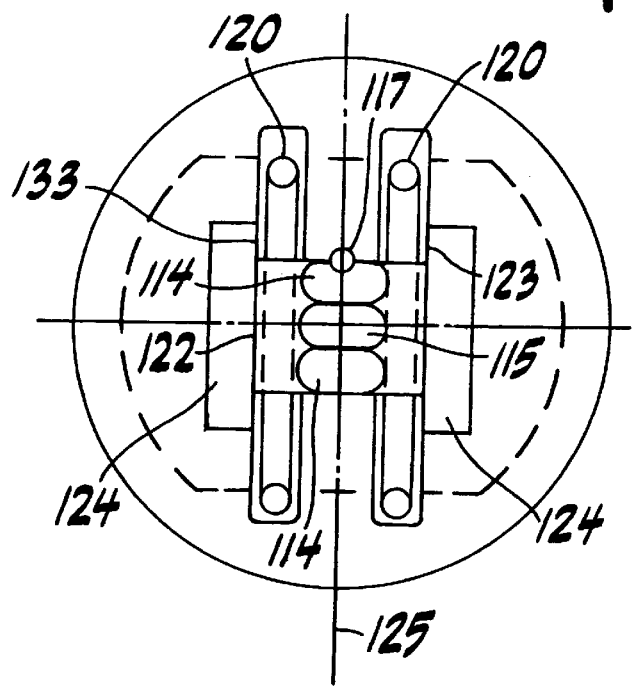
FIG. 5 is an end view of the device shown in FIG. 3 through section C—C.

As shown in FIG. 5, tabs 114 may be located above and below balloon insertion lumen 115, with the tabs 114 illustrated extending distally out of the page toward the viewer, while the balloon insertion lumen 115 extends proximally into the page through main body 110. Flashback lumen 117 is adjacent to one of the tabs 114 and the staples 120 are located substantially symmetrically about a center line 125 of the tubular projection 105. A staple bending stop 122 adjacent to the staple lumen 123 is centrally located around the balloon insertion lumen 115. When a staple 120 is pushed (from behind) by staple pusher 121, staple 120 bends (forward) around staple bending stop 122. Continued pushing brings ramps 128 of staple pusher 121 into contact with staple 120 which causes the bent staple 120 to be pushed laterally outward from center line 125 so that the staple 120 is ejected through staple exit lumen 124.

Figure 6:
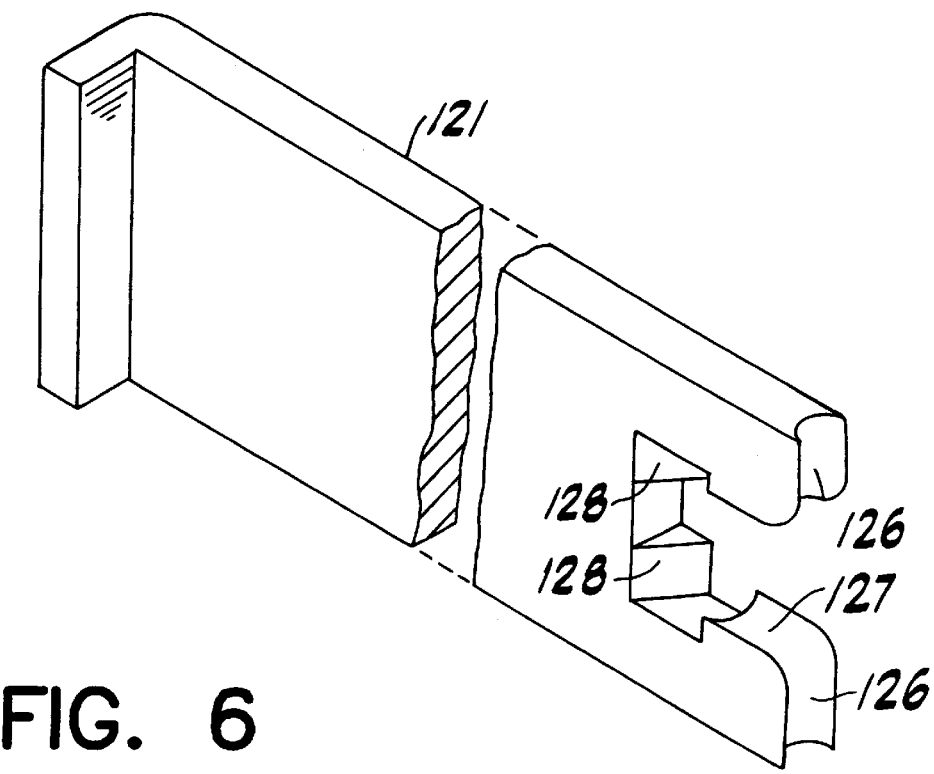
FIG. 6 is a perspective view of the staple pusher according to the first embodiment of the invention.

As shown in FIG. 6, the proximal end of staple pusher 121 is connected to trigger 112. The distal end of staple pusher 121 has a stylized shape that allows staple pusher 121 to carry out its stapling function. Lateral grooves 126 initially contact staple 120 when trigger 112 is held in the cocked or ready position. When trigger 112 is activated, lateral grooves 126 apply pressure on staple 120 and begin to bend staple 120 about staple bending stop 122. Continued pushing by staple pusher 121 brings longitudinal grooves 127 into contact with staple 120 to complete the bending process.

Staple pusher 121 has ramps 128 which contact a bent staple 120 at the end of the stroke of trigger 112. Ramps 128, by virtue of their wedgelike shape, displace staple 120 around staple bending stop 122 and thereby cause staple 120 to pass through staple exit lumen 124 and ultimately be released from device 1.

Figure 7:
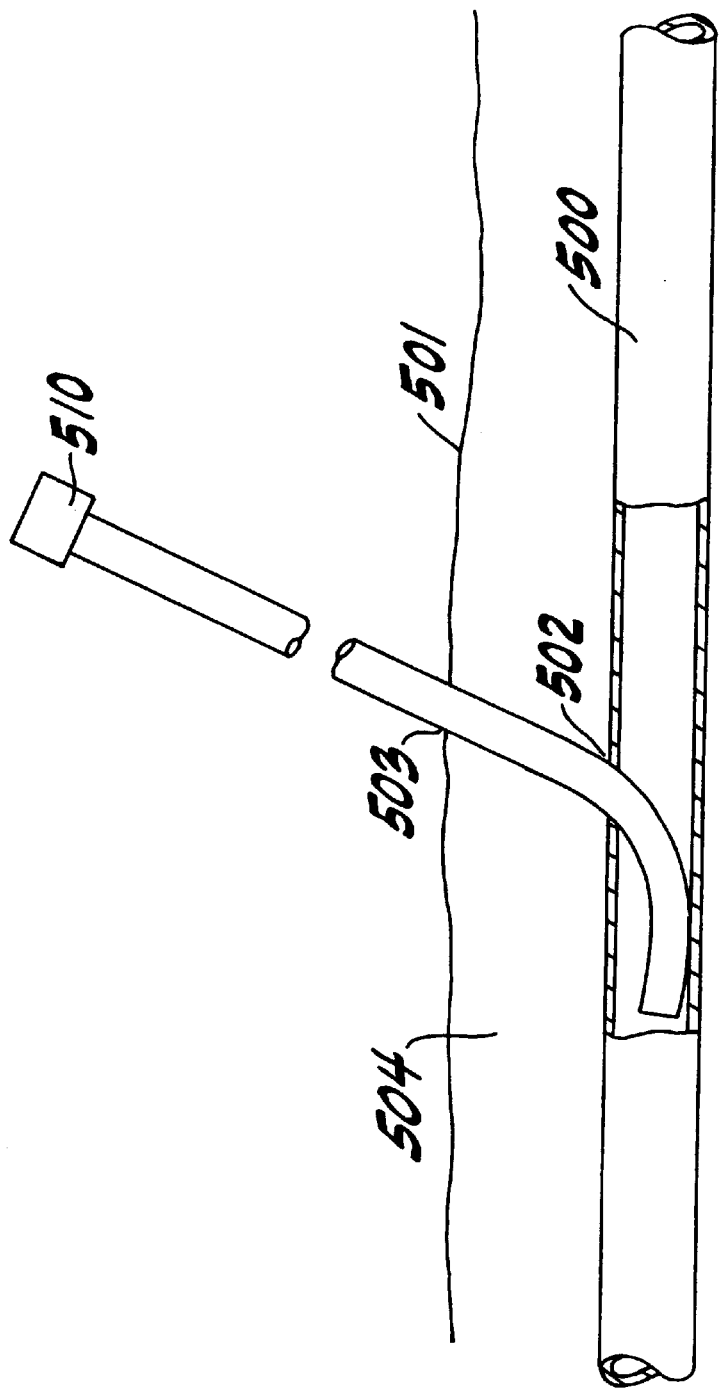
FIG. 7 shows an environment of use of the invention.
Figure 8:
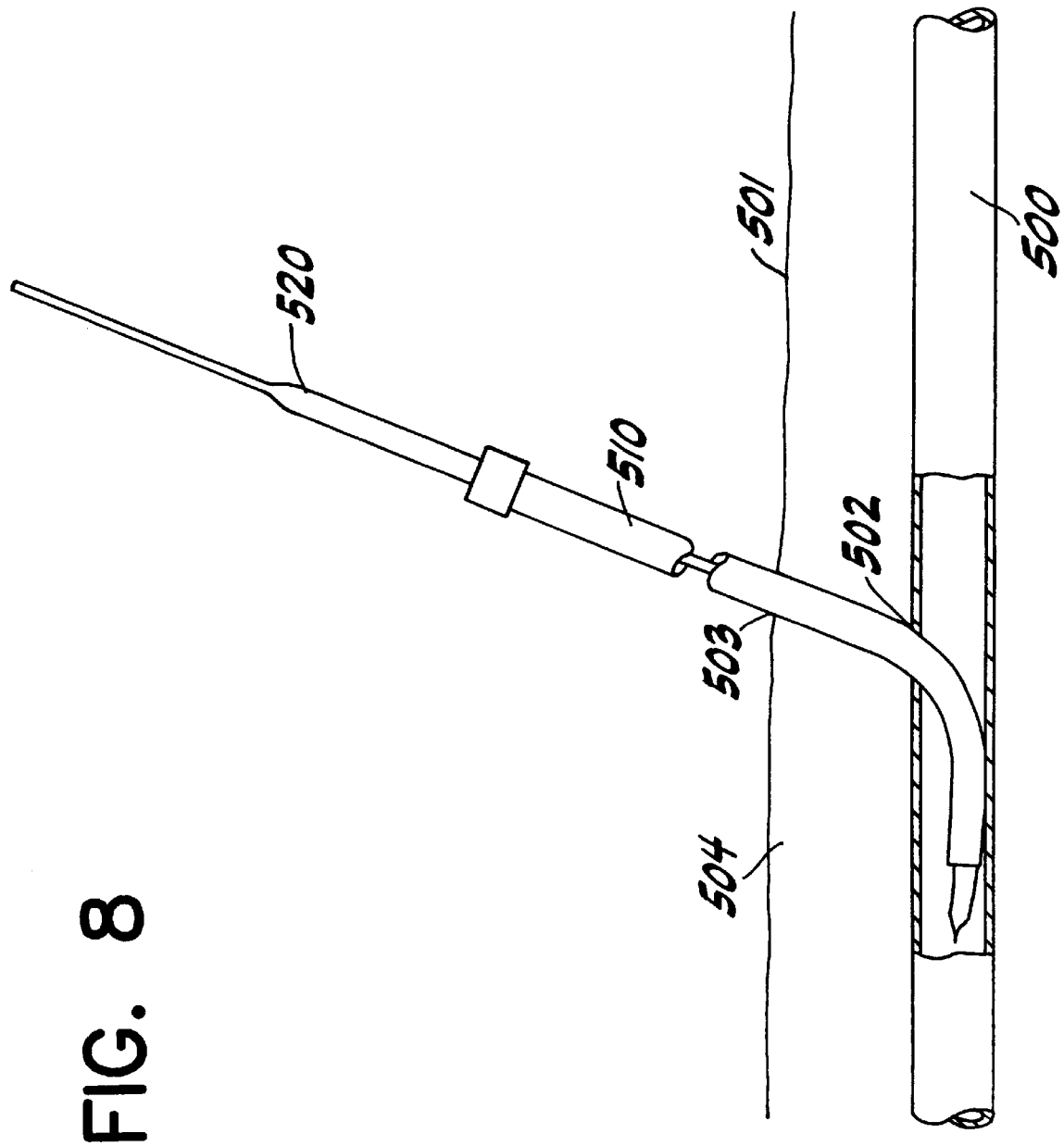
FIG. 8 shows the environment of use further including a balloon catheter.

Having described the mechanical functionality of arterial stapling device 1, a functional use within a living patient will be discussed. FIG. 7 shows an environment for the use of device 1. It is common for medical procedures to employ a procedure sheath 510, also called an introducer. Procedure sheath 510 penetrates the skin line 501 at skin opening 503 and passes through tissue 504 to enter artery 500 at puncture site 502. Through a longitudinal bore in procedure sheath 510, medical instrumentation may be inserted into artery 500. For example, as shown in FIG. 8, a balloon catheter 520 is inserted through procedure sheath 510 to thereby gain a position within artery 500 and tissue 504.

Figure 9:
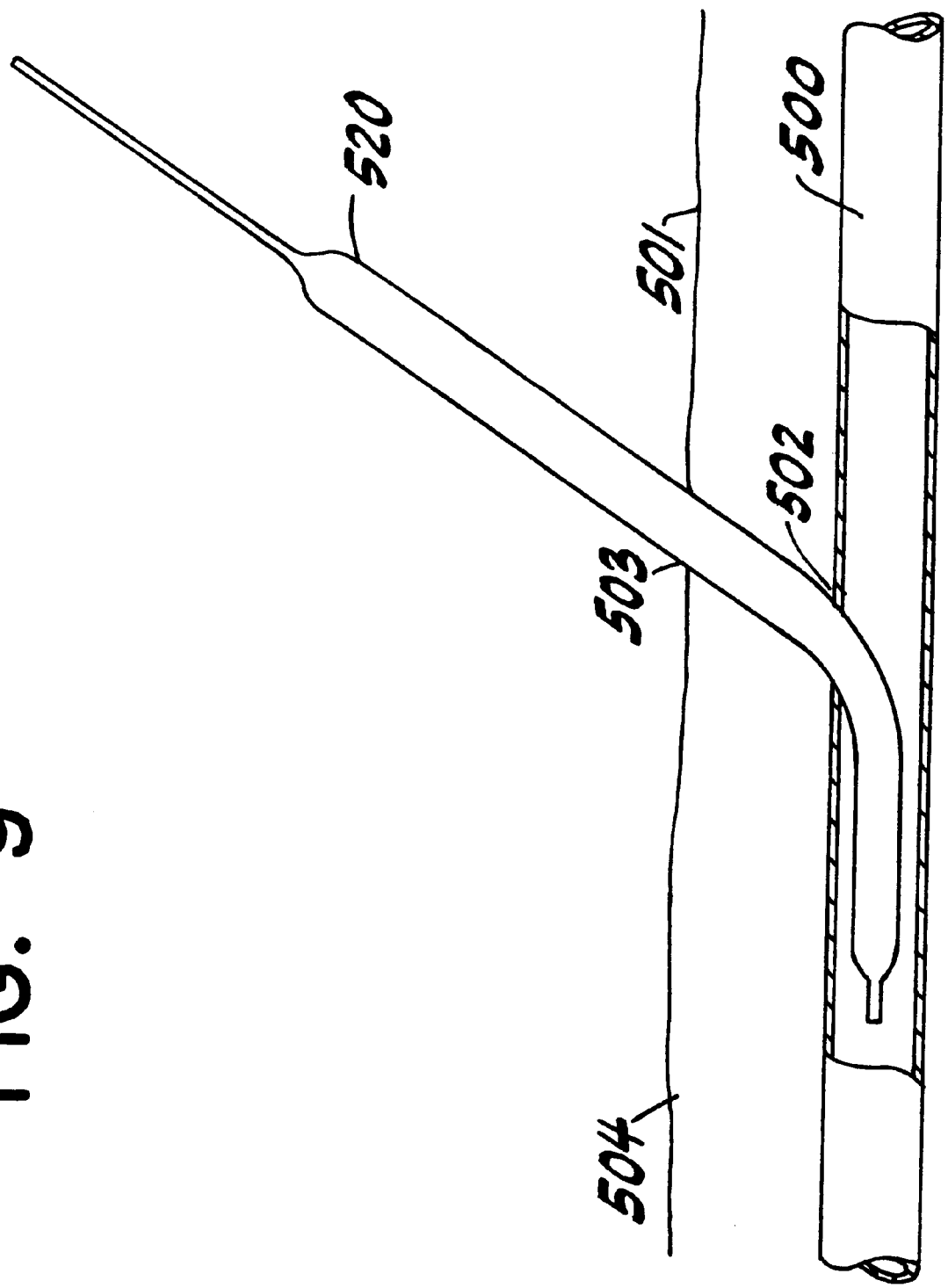
FIG. 9 shows the environment of use with the procedure sheath removed.

As shown in FIG. 9, procedure sheath 510 may be removed from the procedure site while leaving balloon catheter 520 in place. Device 1 of the invention works in conjunction with a balloon catheter 520 which has been placed in artery 500. An appropriate inflation pressure for balloon catheter 520 for use in veins, arteries, and the like will depend upon the particular application and may range from approximately 1 to 50 PSI.

FIG. 10 shows device 1 positioned by sliding the device 1 over balloon catheter 520 via balloon insertion lumen 115. With device 1 inserted over the balloon catheter, removable hub 150 can be applied to the external end of balloon catheter 520. Removable hub 150 includes a balloon inflation port 151, to which an external supply of saline or other suitable media (not shown) is attached in order to pressurize and inflate balloon catheter 520. One advantageous feature of the invention is that, when inflated, the balloon catheter 520 substantially seals the puncture site, reducing bleeding before the actual stapling process occurs.

Device 1 must be inserted under the skin line 501 and through tissue 504 so that the distal end of the tubular projection 105 is flush with the wall of artery 500. If optional tabs 114, which extend distally from the distal end of the tubular projection 105, are included, they may extend into the artery 500. When device 1 is properly inserted, blood entry port 118 receives blood from artery 500. The blood traverses through flashback lumen 117 to blood exit port 119 and thereby indicates to the user that device 1 is properly positioned for stapling.

FIG. 11 shows the distal end of device 1 positioned appropriately in artery 500. Tabs 114 are in artery 500 so that blood flows into blood entry port 118 through flashback lumen 117, to indicate that the device is properly positioned in artery 500. Staple 120 is shown in its bent position. When staple 120 is bent by staple pusher 121, it penetrates artery 500 and, upon continued bending, it also penetrates and deflates balloon catheter 520. The deflated balloon catheter 520 may then be withdrawn through the now sealed puncture, into the balloon insertion lumen 115 while device 1 remains in place adjacent artery 500. To assist in this puncture and removal, balloon catheter 520 may preferably be made of a material that easily tears axially. Thus, balloon catheter 520 tears around staple 120 and is therefore easily removed from the procedure site.

An alternative procedure would allow balloon catheter 520 to be removed prior to being punctured by staple 120. For example, when staple 120 penetrates artery 500, but before it penetrates balloon catheter 520, balloon catheter 520 may be deflated and removed from the puncture site through balloon insertion lumen 115. Staple 120 may then be inserted the rest of the way into artery 500 to complete the procedure.

Figure 12:
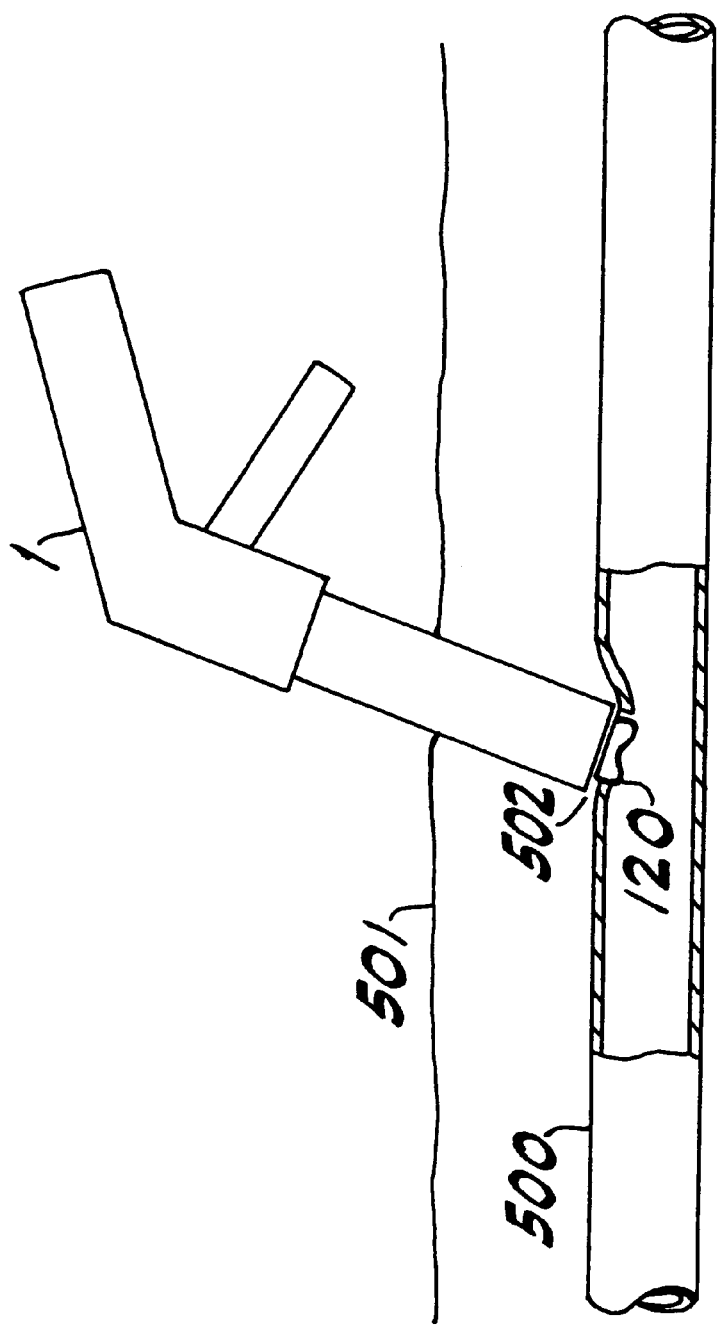
FIG. 12 shows the first embodiment of the invention with a staple placed in an artery according to the invention.

FIG. 12 shows device 1 after staple 120 has been fully ejected from device 1 through activation of the staple pusher 121 as discussed above. Tabs 114 are not depicted in this view in order to show an unobstructed view of the stapled puncture site. Staple 120 clamps the puncture site closed with no other foreign matter left within artery 500. When the staple 120 is released from staple exit lumen 124 (FIG. 5), device 1 may be removed from the puncture site 502.

FIG. 13 shows the puncture site 502 after device 1 has been removed. Two staples 120 are arranged across the puncture site 502, thereby holding the puncture in artery 500 closed. Of special importance is the ability of a user to properly orient the device relative to artery 500 in order to properly place staples 120. For example, as shown, staples 120 are aligned longitudinally with respect to the axis of artery 500. Alternatively, a user may place staples 120 at other orientations relative to artery 500 by positioning device 1 as desired before activating trigger 112. The user must be cognizant of both the anatomy of the living body (i.e. the position and orientation of the artery 500 within the living body) and the position and orientation of the stapling device in order to properly orient the staples 120 with respect to the puncture site 502.

Figure 14:
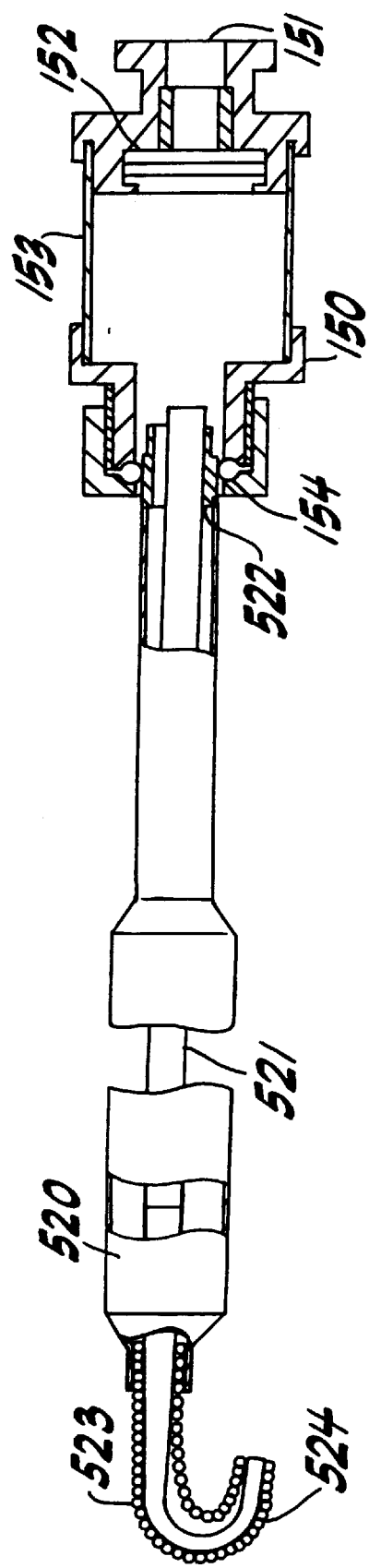
FIG. 14 shows a side view of a removable hub according to the present invention joined to a balloon catheter.

FIG. 14 shows a side view of balloon catheter 520 joined with removable hub 150. Hub 150 is initially coupled to the balloon catheter 520 after the balloon catheter 520 has been inserted through the balloon insertion lumen 115 of device 1. In FIG. 14, the balloon catheter 520 and hub 150 are shown, for example, after the balloon catheter 520 has been removed from the puncture. If the balloon catheter 520 is to be removed from the puncture site without being deflated by the staples 120 (as discussed with reference to FIG. 11), the wide portion of balloon catheter 520 will have to decrease in size to fit into balloon insertion lumen 115. This can be accomplished by accumulator 153 of removable hub 150. As balloon catheter 520 is drawn into balloon insertion lumen 115, the fluid in balloon catheter 520 flows out of balloon catheter 520 into accumulator 153 which is pressure expandable, i.e., when a volume of fluid flows into accumulator 153, the volume of accumulator 153 is expanded to maintain a constant pressure. Thus, balloon catheter 520 may be removed through balloon insertion lumen 115 while maintaining a constant system pressure throughout both balloon catheter 520 and removable hub 150.

As shown in FIG. 14, removable hub 150 may be removably joined to balloon catheter 520 by a compression seal 154. Once joined, fluid may be added to the removable hub 150 (and hence to balloon catheter 520) through its balloon inflation port 151 which includes a check valve diaphragm 152.

A preferred arrangement for the use of balloon catheters generally includes a support wire 521 which is connected to the proximal end of balloon catheter 520 at attachment point 522. At the distal end of balloon catheter 520, the support wire 521 tapers to allow flexibility and is inserted into a spring coil or plastic sleeve 523 which is formed into a "J" shaped tip 524 which allows safe and convenient insertion into arteries and such as is known in the art.

Figure 15:
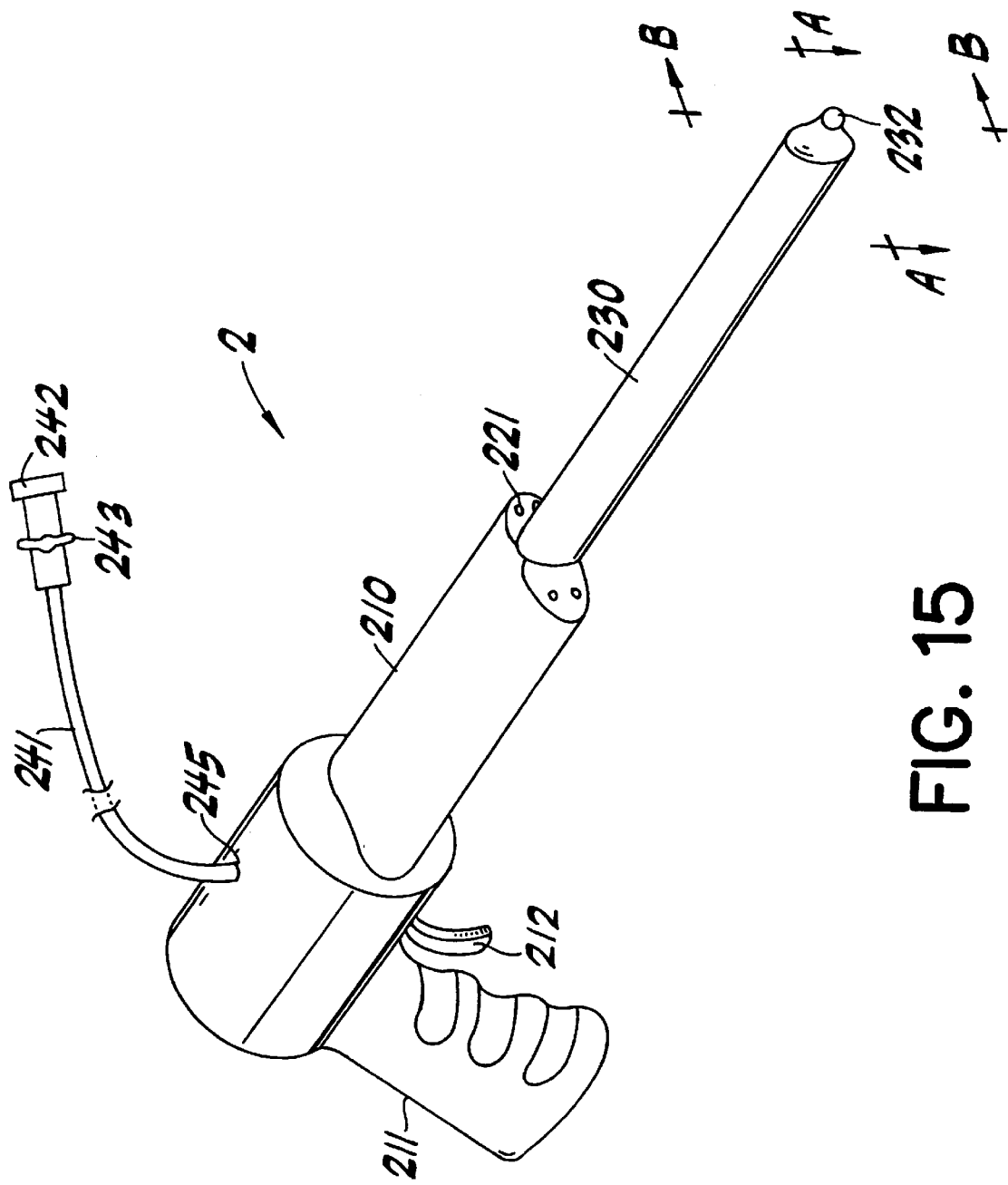
FIG. 15 is a perspective view of a second embodiment of the invention.

A second embodiment of the invention will be discussed in reference to FIG. 15 through 23. FIG. 15 shows a perspective view of the second embodiment of the invention, wherein the device is generally designated by the numeral 2. Device 2 has a main body 210 having, at is proximal end, a handle 211 and a trigger 212. Main body 210 houses staples 220. When device 2 is appropriately positioned for stapling, activation of trigger 212 bends the staples into a desired configuration and ejects the staples 220 from the staple ports 221, in any suitable manner, such as was discussed with reference to the first embodiment of this invention.

An elongated inflatable body 230 extends distally from the distal end of main body 210. Inflatable body 230 is formed of a pliable membrane which includes internal passages. One such passage is guide wire lumen 231, to which access is provided by guide wire inlet 232 which is located at the distal end of the inflatable body 230.

Inflatable body 230 is pressurized by a supply of saline solution or other suitable media (not shown). The solution may be introduced through a supply tube 241 coupled to the supply by port 242 which has a valve 243 to control the flow of the pressurized media. The supply tube 241 may be attached to device 2 by any suitable manner at supply orifice 245.

Figure 20:
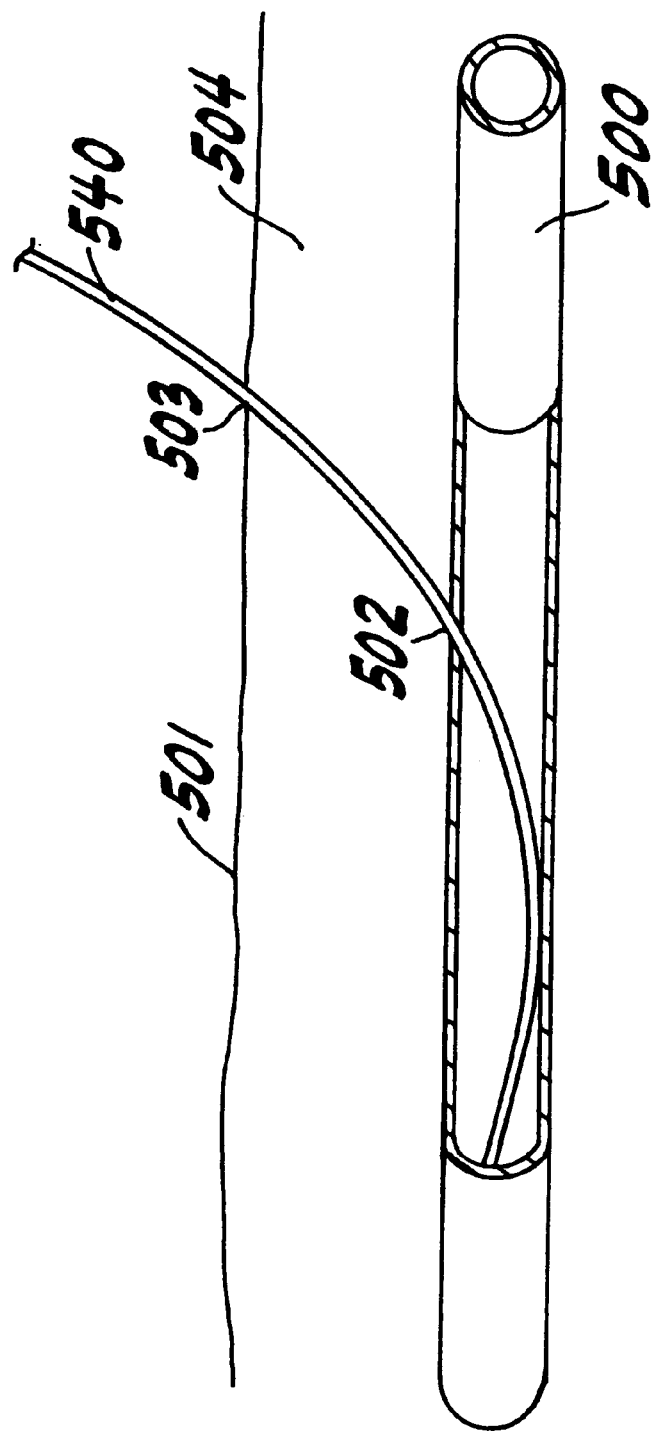
FIG. 20 shows an environment of use of the device.
Figure 21:
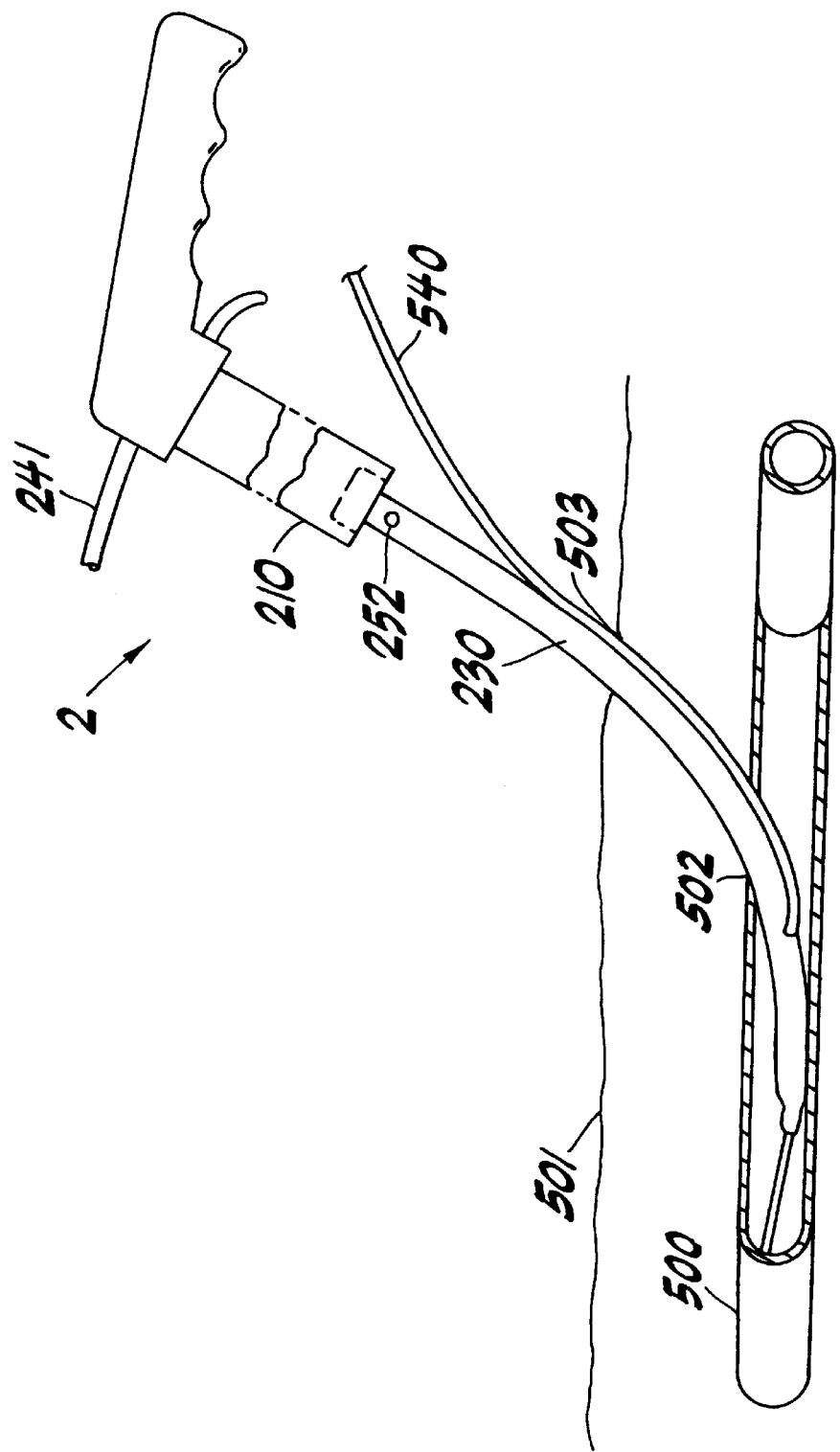
FIG. 21 shows an embodiment of the device with the inflatable body portion partially inserted into an artery in a living body.

FIGS. 16 and 17 show device 2 containing internal passages 240, 231, 250 of device 2, which are used for inflating inflatable body 230, providing passage of the guide wire, and other purposes, such as allowing passage of blood to indicate the position of device 2 within artery 500 (shown in FIGS. 20 and 21). Main body 210 contains pressure supply passage 240 to which supply tube 241 connects at the proximal end of main body 210. Pressure supply passage 240 has a supply outlet 244 at the interface between main body 210 and inflatable body 230.

Main body 210 also contains a flashback lumen 250 which has a blood exit port 251 on the exterior of main body 210 and a blood entry port 252 on the proximal end of the inflatable body 230. When blood entry port 252 is located within artery 500, blood will enter the blood entry port 252, pass through flashback lumen 250, and exit the blood exit port 251. When blood exits the blood exit port 251, the attending physician or other user of device 2 will know that the blood entry port 252 is located within artery 500. Knowing the relative position of device 2 within artery 500, the user can determine when to activate trigger 212 to insert staples 220. A portion of flashback lumen 250 is located in main body 210 and a portion is located in inflatable body 230. The portion of flashback lumen 250 in inflatable body 230 is delimited by an adhesive barrier 253 which occludes flashback lumen 250.

As shown in FIG. 17, supply tubing 241 may be attached to the pressure supply passage 240 at the proximal end of main body 210. Pressure supply passage 240 is connected with inflatable body 230 at the interface of main body 210 and is connected to inflatable body 230 at supply outlet 244.

Flashback lumen 250 extends from the proximal end of main body 210 through a portion of inflatable body 230 and to a blood inlet port 252. An adhesive barrier 253 located on the distal side of the port 252, seals the flashback lumen 250. At the distal end of inflatable body 230, guide wire inlet 232 provides access for a guide wire to enter guide wire lumen 231. Guide wire lumen 231 is provided with guide wire exit port 233 proximal to guide wire inlet 232. An adhesive barrier 234 separates guide wire lumen 231 from the other internal passages of inflatable body 230.

Figure 18:
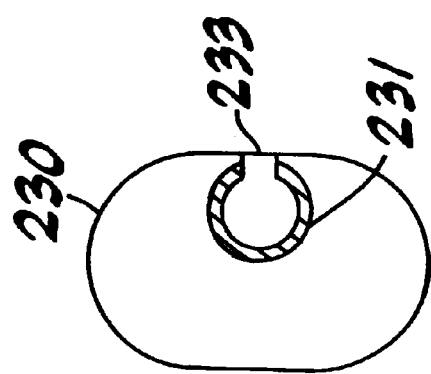
FIG. 18 is an end view of the device shown in FIG. 17 through section C—C.

As shown in FIG. 18, inflatable body 230 contains guide wire lumen 231 having a guide wire exit port 233, separated from the proximal end of inflatable body 230 by a predetermined distance. According to a still further embodiment of the invention, guide wire exit port 233 may be located on main body 210, wherein the guide wire enters inflatable body 230 via a guide wire inlet 232, located at the proximal end of the inflatable body 230, and remains within the inflatable body 230 for its entire length.

Figure 19:
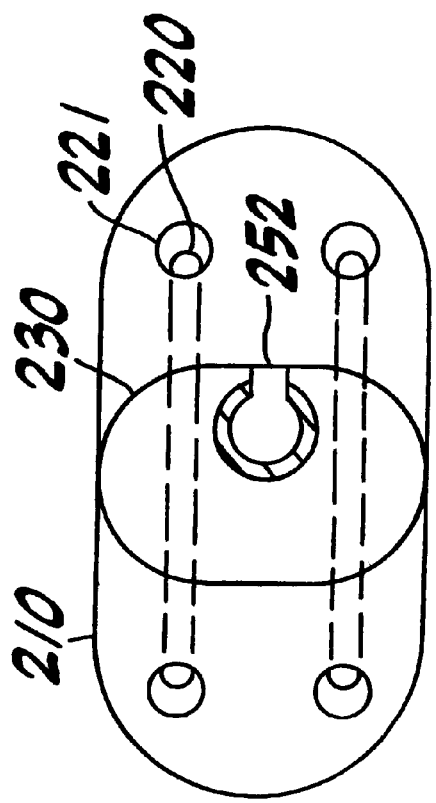
FIG. 19 is an end view of the device shown in FIG. 17 through section D—D.

As shown in FIG. 19, the distal end of main body 210 holds staples 220 within the staple openings 221. It is further shown that inflatable body 230 contains flashback lumen 250 and that a blood entry port 252 is located on the side of inflatable body 230.

FIG. 20 shows an environment of use for the arterial stapling device 2. Artery 500 is located within a living body below the surface of the skin 501. A guide wire 540, which may be used for numerous medical procedures, is shown penetrating the skin 501 at skin opening 503, passing through tissue 504, and entering artery 500 at puncture site 502.

FIG. 21 shows the arterial stapling device 2 partially inserted into artery 500. In the position shown, guide wire 540 is inserted into guide wire lumen 231 of inflatable body 230 with the inflatable body 230 penetrating artery opening 502 by being moved along the path as guided by guide wire 540.

Figure 22:
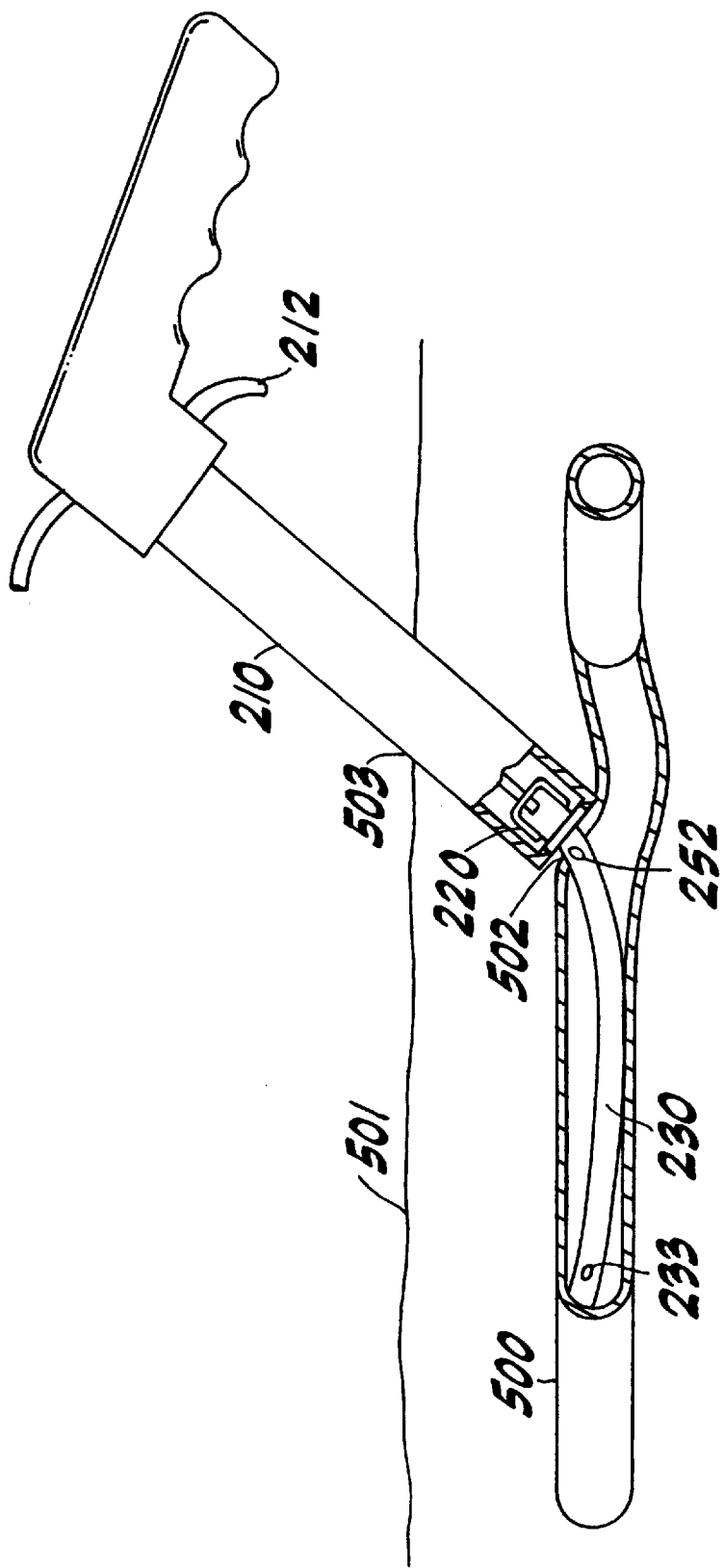
FIG. 22 shows an embodiment of the device with the inflatable body portion fully inserted into the artery so that the device is in position to staple the artery.

FIG. 22 shows device 2 in the position at which staple 220 may be inserted into artery 500. Preferably before activating trigger 212, guide wire 540 should be withdrawn from the artery and thus from guide wire lumen 231 of device 2. As shown in FIG. 22, guide wire 540 has been removed entirely from the environment, having been withdrawn from guide wire lumen 231, from artery opening 502, and from the skin opening 503.

The inflatable body 230 is inserted into artery 500 such that blood entry port 252 is inside artery 500. Such a position allows blood to enter flashback lumen 250 through blood entry port 252, and exit through blood exit port 251. The flow of blood through flashback lumen 250 provides the user of device 2 with information about the position of device 2 relative to artery 500.

An advantageous feature of the invention is that artery 500 is provided with support from inflatable body 230, which thereby facilitates insertion of staples 220 into the wall of artery 500. By selection of an appropriately sized and shaped inflatable body 230, artery 500 may be sufficiently filled by the inflatable body 230 to thereby seal off blood flow during the stapling procedure. It may be desirable to have an inflatable body 230 which has a different, e.g. smaller, diameter where it will resid in the artery, than it does where it will support the artery near the puncture site 502.

Figure 23:
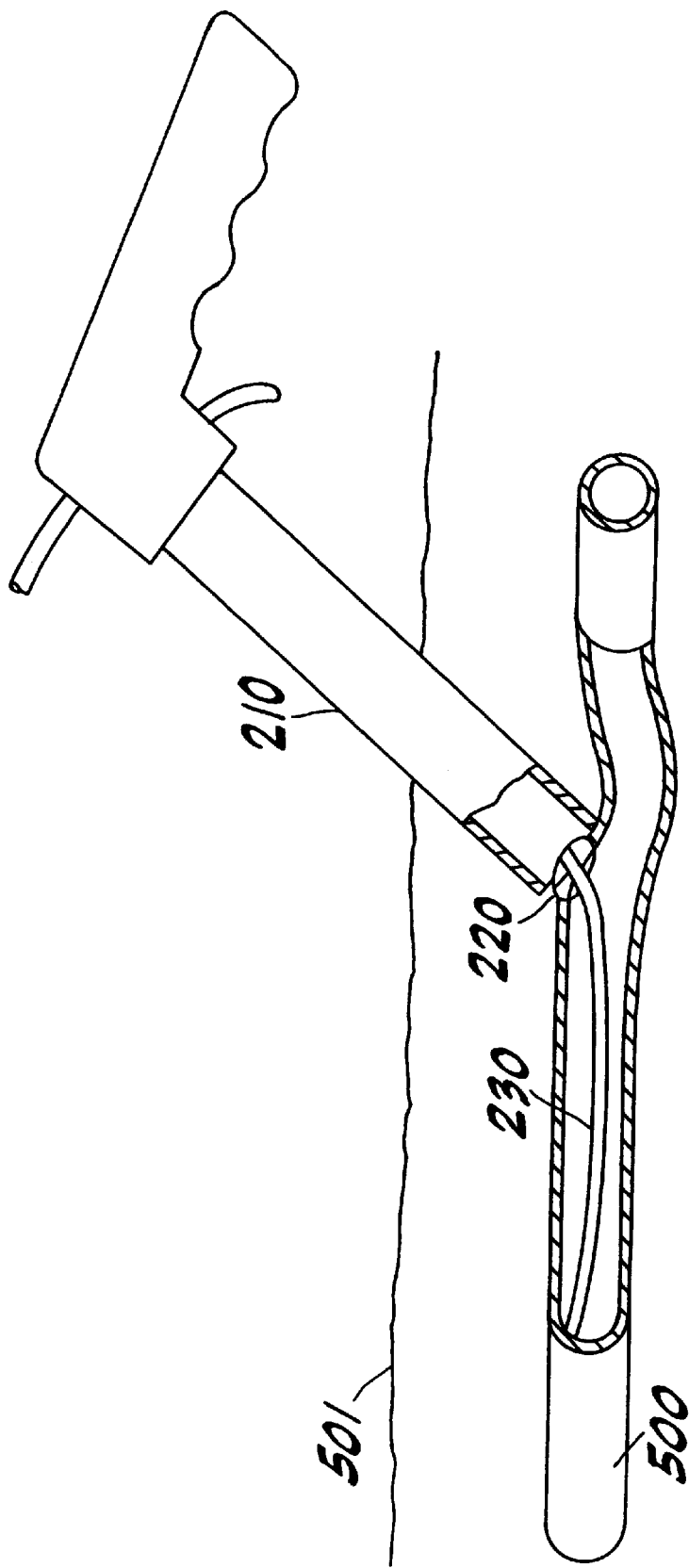
FIG. 23 shows the trigger has been activated and the staple is in place in the artery.

FIG. 23 shows device 2 after trigger 212 has been activated and staple 220 is in place in artery 500. Staple 220 penetrates the wall of artery 500 as well as inflatable body 230, thereby deflating it.

Inflatable body 230 is made of such a material that when it is punctured by staple 220, the material rips longitudinally in order to be pulled through staple 220 for removal from artery 500. Thus, no foreign material is left in artery 500 after the deflated inflatable body 230 has been pulled through staple 220.

Those skilled in the art will understand that staple size and dimensions of the device may be determined by the application to which it is applied. For example, in relatively small arteries, relatively small components must be used, whereas, for larger arteries, a device having relatively larger components may be appropriate. The balloon catheter over which a first embodiment of the device is applied, or the inflatable body portion of a second embodiment of the device, can be relatively short or long depending on the specific procedure.

Because the present invention is capable of various modifications and alternate constructions, the specification is not intended to limit the invention to the specific embodiments disclosed herein. Rather, it is intended to be limited only by the claims appended hereto.

What is claimed is:

1. A device for sealing a wall opening in a wall of an anatomical structure within a living body comprising:

a housing extending from a distal end to a proximal portion, the housing including a catheter receiving lumen extending therethrough from a first opening formed in the proximal portion to a second opening formed in the distal end, wherein when the device is in an operative position with a catheter extending through the catheter receiving lumen and into the wall opening, the distal end is located within the living body adjacent to the wall opening and the proximal portion remains outside the living body, and wherein the housing defines at least a first staple orifice in the distal end adjacent to the second opening so that, when the device is in the operative position, the first staple orifice extends across a portion of the wall opening;

a stapling mechanism mounted within the housing adjacent to the first staple orifice, the stapling mechanism adapted to, upon operation, puncture an inflatable member coupled to the distal end of the housing, by ejecting a staple from the first staple orifice and into the inflatable member;

an actuating mechanism coupled between the proximal portion of the housing and the stapling mechanism, the actuating device adapted to operate the stapling mechanism.

2. The device according to claim 1, wherein the housing further includes a second staple orifice, the first staple orifice and the second staple orifice being adjacent to the second opening, wherein when the device is in the operative position, each of the first and second staple orifices extends across a respective portion of the wall opening.

3. The device according to claim 2, wherein the second staple orifice is substantially parallel to the first staple orifice.

4. The device according to claim 3, wherein the first staple orifice is on a first side of the second opening and the second staple orifice is on a second side of the second opening, the first and second sides of the second opening being opposite one another.

5. The device according to claim 2, wherein the actuating mechanism further includes:

a plurality of triggers disposed on the proximal portion of the housing, each trigger being individually actuatable, wherein activation of one of the triggers emits a staple from a respective one of the first and second staple orifices.

6. The device according to claim 1, wherein the housing further includes:

a flashback lumen extending within the housing from a fluid entry port formed on the distal end of the housing to a fluid exit port formed on the proximal portion of the housing.

7. The device according to claim 1, wherein the housing further includes:

at least one tab extending distally from the distal end of the housing adjacent to the second opening so that when a balloon catheter extends through the catheter receiving lumen, the tab provides support for the balloon catheter, and wherein, when the device is in an operative position, the at least one tab penetrates the wall opening.

8. The device according to claim 7, wherein the at least one tab is selectively coupleable to and removable from the housing.

9. The device according to claim 7, wherein one of the at least one tabs is adjacent a fluid entry port, wherein the tab includes a fluid channel formed on a surface thereof, wherein a proximal end of the fluid channel is in fluid communication with the fluid entry port.

10. A method for sealing an opening in the wall of an anatomical structure within a living body comprising the steps of:

inserting a balloon catheter into the living body so that a distal end of the balloon catheter extends through the opening while a proximal portion of the balloon catheter is received in the opening;

inflating the balloon catheter to seal the opening;

guiding a stapling device along the balloon catheter until the device is located in a desired position adjacent to the opening, wherein, when the device is received on the balloon catheter in the desired position, a staple ejection port of the device straddles a portion of the opening;

operating the stapling device so that a staple is ejected from the device, penetrates the wall of the anatomical structure, pierces the balloon catheter and is bent into a closed configuration to seal the opening; and withdrawing the balloon catheter and the device from the living body.

11. A method for sealing a wall opening in a wall of an anatomical structure within a living body comprising the steps of:

inserting an apparatus for sealing a wall opening in a wall of an anatomical structure into a desired position within the living body wherein the apparatus includes an inflatable structure which, when the device is in the desired position, extends from a housing of the apparatus into the wall opening and, wherein the apparatus further includes a stapling mechanism which, when the device is in the desired position, is located adjacent to the opening;

inflating the inflatable member to seal the wall opening;

operating the stapling mechanism to place at least one staple into the wall of the anatomical structure across a portion of the opening, wherein the at least one staple penetrates the inflatable structure, and wherein the stapling mechanism operates to form the staple into a sealing configuration that draws the sides of the wall opening together to seal the wall opening; and withdrawing the apparatus from the living body.

12. The method according to claim 11 wherein the stapling mechanism is operated so that the at least one staple penetrates the wall of the anatomical structure.

13. A method of sealing a wall opening in a wall of an anatomical structure within a living body comprising the steps of:

placing the distal end of a balloon catheter into the anatomical structure wherein a proximal portion of the balloon catheter is accessible outside the living body;

placing a stapling device onto the proximal end of the balloon catheter by inserting the balloon catheter through an insertion lumen of the stapling device;

inflating at least a portion of the balloon catheter with a pressurizing medium;

guiding the stapling device into an operative position by moving the device along the balloon catheter so that a distal end of the stapling device is adjacent to the wall opening;

orienting the stapling device relative to the anatomical structure such that the stapling device emits staples in a desired orientation relative to the anatomical structure;

actuating the stapling device to place at least one staple into the anatomical structure so that the staple extends across at least a portion of the wall opening;

removing the balloon catheter from the anatomical structure by withdrawing it through the wall opening; and removing the stapling device from the anatomical structure.

14. The method according to claim 13 wherein the step of guiding the device to an operative position further includes:

moving the stapling device along the balloon catheter until fluid from the anatomical structure enters a fluid entry port of a flashback lumen and passes through the flashback lumen to a fluid exit port.

15. The method according to claim 13 further including the steps of:

operating the stapling device so that when the stapling device is actuated, the staple penetrates and deflates the balloon catheter; and removing the balloon catheter from the anatomical structure by tearing the balloon catheter away from the staple longitudinally.

16. A device for sealing a wall opening in a wall of an anatomical structure within a living body comprising:

a housing extending from a distal end to a proximal portion, the housing including a catheter receiving lumen extending therethrough from a first opening formed in the proximal portion to a second opening formed in the distal end, the housing defining a first staple orifice in the distal end adjacent to the second opening;

an inflatable member coupled to the distal end, wherein when the device is in an operative position with a catheter extending through the catheter receiving lumen and into the wall opening, the distal end is located within the living body adjacent to the wall opening with the first staple orifice extending across at least a portion of the wall opening, the proximal portion remains outside the living body and the inflatable member extends within the anatomical structure;

a stapling mechanism mounted within the housing adjacent to the first staple orifice so that a staple ejected from the first staple orifice by the stapling mechanism punctures the inflatable member; and an actuating mechanism coupled between the proximal portion of the housing and the stapling mechanism.

* * * * *